(12) United States Patent
Domnich et al.

(10) Patent No.: US 11,903,854 B2
(45) Date of Patent: Feb. 20, 2024

(54) IMPLANTATION DEVICE

(71) Applicant: VesselSens GmbH, Bonn (DE)

(72) Inventors: Alexej Domnich, Bonn (DE); Saad Salem, Bonn (DE)

(73) Assignee: VesselSens GmbH, Bonn (DE)

( * ) Notice: Subject to any disclaimer, the term of this patent is extended or adjusted under 35 U.S.C. 154(b) by 660 days.

(21) Appl. No.: 17/041,939

(22) PCT Filed: Mar. 27, 2019

(86) PCT No.: PCT/EP2019/057733
§ 371 (c)(1),
(2) Date: Sep. 25, 2020

(87) PCT Pub. No.: WO2019/185724
PCT Pub. Date: Oct. 3, 2019

(65) Prior Publication Data
US 2021/0045904 A1    Feb. 18, 2021

(30) Foreign Application Priority Data

Mar. 28, 2018   (DE) .................... 20 2018 101 750.0

(51) Int. Cl.
| | |
|---|---|
| *A61F 2/95* | (2013.01) |
| *A61F 2/962* | (2013.01) |
| *F16H 1/22* | (2006.01) |
| *F16H 25/20* | (2006.01) |
| *A61F 2/966* | (2013.01) |

(52) U.S. Cl.
CPC ............ *A61F 2/9517* (2020.05); *A61F 2/962* (2013.01); *A61F 2/966* (2013.01); *F16H 1/227* (2013.01); *F16H 25/20* (2013.01); *F16H 2025/2053* (2013.01); *F16H 2025/2062* (2013.01)

(58) Field of Classification Search
CPC ........ A61F 2/9517; A61F 2/962; A61F 2/966; A61F 2250/0097; F16H 1/227; F16H 2025/2053; F16H 2025/2062; F16H 25/20
See application file for complete search history.

(56) References Cited

U.S. PATENT DOCUMENTS

| | | | |
|---|---|---|---|
| 2003/0074045 A1* | 4/2003 | Buzzard | ................... A61F 2/95 623/1.11 |
| 2006/0282150 A1 | 12/2006 | Olson et al. | |
| 2013/0158655 A1* | 6/2013 | Sutton | ................... A61F 2/2427 604/95.04 |
| 2020/0367769 A1 | 11/2020 | Domnich et al. | |
| 2021/0022610 A1 | 1/2021 | Domnich et al. | |

OTHER PUBLICATIONS

European Patent Office, International Search Report in International Application No. PCT/EP2019/057733 (dated Jun. 25, 2019).
European Patent Office, Written Opinion in International Application No. PCT/EP2019/057733 (dated Jun. 25, 2019).
International Bureau of WIPO, International Preliminary Report on Patentability in International Application No. PCT/EP2019/057733 (dated Sep. 29, 2020).

* cited by examiner

*Primary Examiner* — Mohamed G Gabr
(74) *Attorney, Agent, or Firm* — Leydig, Voit & Mayer, Ltd.

(57) ABSTRACT

The invention relates to an implantation device for implanting a vascular implant, which enables a vascular implant to be easily positioned and to be discharged in a slip-free manner.

12 Claims, 3 Drawing Sheets

IMPLANTATION DEVICE

CROSS-REFERENCE TO RELATED APPLICATIONS

This patent application is the U.S. national phase of International Application No. PCT/EP2019/057733, filed on Mar. 27, 2019, which claims the benefit of German Patent Application No. 20 2018 101 750.0, filed Mar. 28, 2018, the disclosures of which are incorporated herein by reference in their entireties for all purposes.

The invention relates to an implantation device for implanting a vascular implant, which enables a vascular implant to be easily positioned and to be discharged in a slip-free manner.

Implantation instruments and catheters are used to insert and position medical implants in vascular systems, for example for use in human medicine. In percutaneous transluminal angioplasty and percutaneous transluminal coronary angioplasty, minimally invasive implants such as stents are advanced via the vessels to the location of the affected vessel portion and applied using implantation instruments (delivery system). For the positioning of the catheter in the vessel, the catheter is selected to have a substantially smaller diameter than the affected vessel with the stricture which the catheter must penetrate. In the case of self-expanding implants such as nitinol stents, a sheath (tube) on the catheter system is used for this. As soon as the catheter system has reached the narrowed portion of the vessel, the sheath is flushed and then pushed backwards relative to the catheter system. The self-expanding stent unfolds above the Af temperature (shape-memory alloy), wherein the Af temperature is selected to be significantly lower than the body temperature.

The relative movement of the sheath on the fixed catheter system is important for the positioning accuracy of the implant in the vessel. Usually, the surgeon fixes the system with one hand and pulls the sheath back with the other, but it often happens that there is a slight relative movement between the sheath and the catheter system, which leads to an incorrect implantation and thus to serious complications.

Particularly in the case of implants which also include sensor functions, the frictional force between the displaceable sheath and the implant is often increased as a result of the geometric properties. As a result, the user has to exert a great deal of force for the discharge process of the sensor system in order to release the implant. In the case of large frictional forces, there can be an undesirable relative movement of the entire catheter system with respect to the sheath, as a result of which the discharge process either fails or takes place incorrectly.

Solutions are known from the prior art which are also used in the cardiovascular field, among others. Such systems are used, for example, for stent grafts or for the implantation of heart valve replacements.

The object of the present invention is to provide an implantation device for implanting a vascular implant which allows a more secure implantation.

The object is achieved by the implantation device described herein. The dependent claims indicate advantageous developments of the implantation device according to the invention.

The object is achieved by the implantation device according to claim 1. The dependent claims indicate advantageous developments of the implantation device according to the invention.

An implantation device for implanting a vascular implant is specified according to the invention. The implantation device according to the invention has an internally toothed gear, which can advantageously be designed in the shape of a cylinder.

The implantation device according to the invention also has one or more transport devices arranged adjacent to one another. Each of the transport devices has a spindle and an externally toothed gear arranged coaxially to the spindle. The externally toothed gear is firmly connected to the spindle. An axis of rotation of the externally toothed gear is advantageously coaxial with an axis around which the spindle is wound. The spindles of all transport devices advantageously have the same helicity.

Particularly advantageously, the spindle and the externally toothed gear of the transport devices can each be carried by a common shaft which is coaxial with the axis of rotation of the externally toothed gear.

The implantation device according to the invention also has at least one adapter which has a number of threads corresponding to the number of transport devices. The threads are advantageously helical internal threads. The thread axes of the threads are advantageously parallel to one another.

In the implantation device according to the invention, the gears of the one or more transport devices are in engagement with the internally toothed gear. In this way, a rotation of the internally toothed gear is transmitted to the externally toothed gears of the transport devices, which in turn cause the spindles to rotate.

According to the invention, the spindles of the one or more transport devices are each in engagement with one of the threads of the adapter. The internal threads of the adapter therefore advantageously each have the same pitch as the spindle that engages in this thread. A rotation of the spindles therefore leads to a movement of the adapter in the direction of the axis of the spindles.

The implantation device according to the invention also has a tubular sheath which is connected to the adapter at one of its ends. A movement of the adapter therefore leads to a movement of the sheath.

In addition, the implantation device has a hypotube which is arranged over at least the length of the spindles, adjacent to the spindles of the one or more transport devices and parallel to them.

The implantation device also has a catheter which is at least partially arranged in the hypotube. The catheter is preferably glued to the hypotube at one of its ends.

In an advantageous embodiment of the invention, the internally toothed gear, the one or more transport devices and the adapter can be arranged in a common housing. The hypotube can then be held at a distal end of the housing and extend at least to an opposite proximal end of the housing. The proximal end is understood to mean that end which, when the implantation device is used as intended, faces the patient. Accordingly, the distal end is that end which, when used as intended, faces away from the patient. The catheter is advantageously connected to the end of the hypotube at which the hypotube is held on the housing.

In an advantageous embodiment of the invention, the hypotube can be inserted into a wing element at the end at which it is held on the housing. The wing element can have a cylindrical recess into which the hypotube is inserted. On an outer circumference of the cylindrical recess, two wing surfaces can be arranged opposite one another with respect to a cylinder axis. The wing element can advantageously have portions which extend beyond the wing elements in the direction of the cylinder axis and which have a circular circumference. The wing element can be mounted in the housing in these portions.

In an advantageous embodiment of the invention, the internal toothing of the internally toothed gear can have 40 teeth and the gear wheel(s) of the one or more transport devices can each have 10 teeth. Such dimensioning enables good power transmission from the internally toothed gear to the externally toothed gear(s) and thus to the spindles.

In a particularly advantageous embodiment of the invention, the housing can have at least two openings through which the internally toothed gear protrudes. In this way, a user of the device can grip and rotate the internally toothed gear. The opening areas of these openings can advantageously be cylindrical and parallel to an outer surface of the internally toothed gear. In particular, it is also possible that the opening areas of the openings coincide with the outer surface of the internally toothed gear in the region of the respective opening. The at least two openings can advantageously be exactly opposite one another with respect to an axis of rotation of the internally toothed gear.

In an advantageous embodiment of the invention, the implantation device can have a counter gear which is arranged inside the internally toothed gear and which is engagement with the teeth of the gears of the transport devices.

The counter gear can be an externally toothed gear. The dimensioning of the counter gear results from the dimensions of the internally toothed gear and the gears of the transport devices. The counter gear can advantageously be arranged coaxially to an axis of rotation of the internally toothed gear.

The implantation device according to the invention preferably has exactly two transport devices. The two transport devices are then particularly preferably arranged opposite one another with respect to the hypotube. The axes of the externally toothed gears and the spindles of these transport devices are advantageously parallel to one another.

In an advantageous embodiment of the invention, the spindles can each be of a length greater than or equal to 80 mm, preferably greater than or equal to 90 mm, particularly preferably greater than or equal to 100 mm and/or less than or equal to 130 mm, preferably less than or equal to 120 mm. The length of the spindles is preferably determined as a function of the length of the implant to be implanted and is preferably at least as long as the length of the implant.

The pitch of the spindles can preferably be greater than or equal to 4 mm, preferably greater than or equal to 5 mm, preferably equal to 6 mm and/or less than or equal to 9 mm, preferably less than or equal to 7 mm.

The spindle can advantageously be designed as a trapezoidal thread.

In an advantageous embodiment of the invention, the tubular sheath can be connected to the adapter via a screw cap and/or a ring with a chamfer.

In an advantageous embodiment of the invention, the housing can have a linear scale on its outer surface. The adapter can then have an element which protrudes through an incision in the housing that extends parallel to the scale, adjacent to the scale. This incision is preferably designed as an elongated slot which is parallel to the hypotube. The element protruding from the housing through the incision then serves as an indicator of the position of the adapter on the scale. In this way, the position of the adapter and thus how far the implant has already been released can be read on the scale.

The internally toothed gear, the one or more transport devices, the adapter and the hypotube, as well as the counter gear (if applicable) are advantageously arranged inside the housing. The housing can have a proximal portion in which the spindles and the hypotube are present and in which the adapter can be displaced. On its distal side, this portion of the housing can be limited by a wall through which the shafts of the transport devices run, so that the spindles are arranged on the proximal side of this wall and the externally toothed gears of the transport devices are arranged on the distal side of this wall. A region of the housing in which the internally toothed gear is arranged can then adjoin the distal side of the wall. This region of the housing can have the described openings through which the internally toothed gear can be rotated by a user.

A region of the housing in which the hypotube and the catheter are held can then connect to the distal side of the internally toothed gear. This region can be tapered relative to the other proximal regions of the housing.

In the following, the invention will be explained by way of example with reference to drawings. The same reference numerals denote the same or corresponding features. The features described in the examples can also be implemented independently of the specific example and combined between different examples.

DETAILED DESCRIPTION OF THE INVENTION

Figure 1:
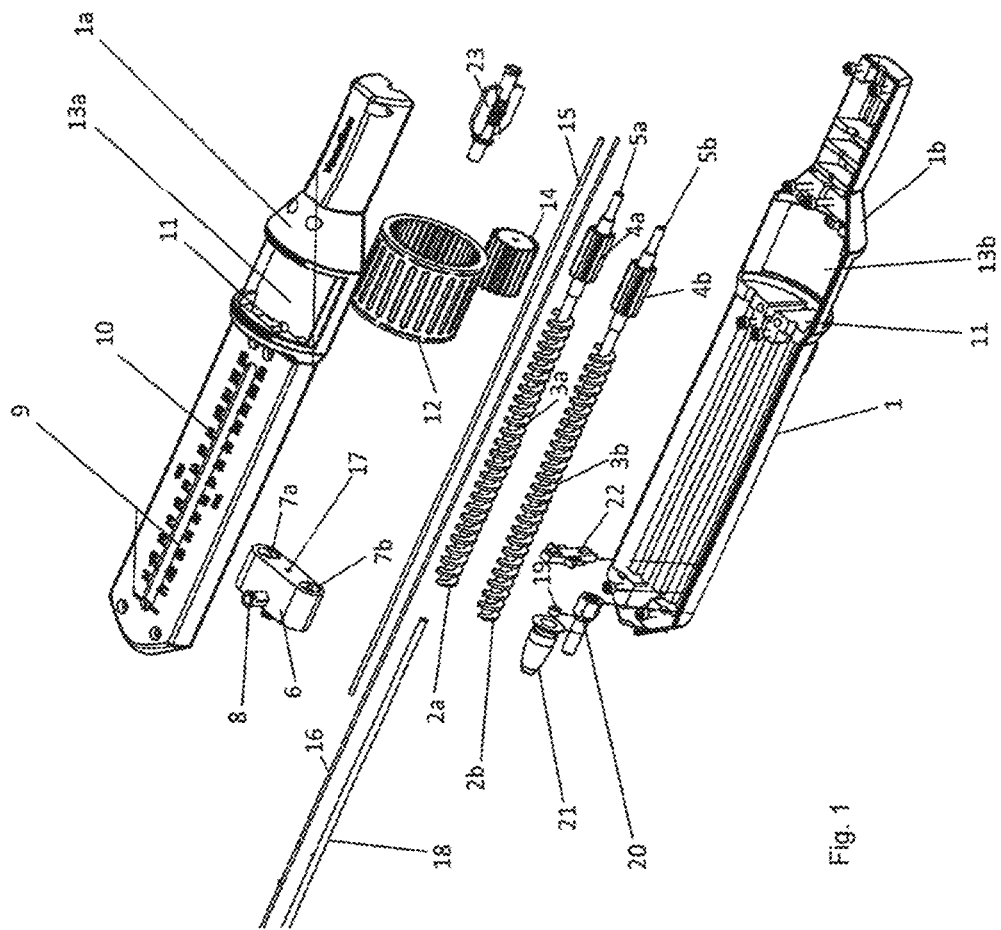
FIG. 1 is an exploded view of an implantation device according to the invention.

FIG. 1 shows an example of an implantation device according to the invention as an exploded drawing. In the example shown, the implantation device has a housing 1 which is designed in two parts here with an upper shell 1*a* and a lower shell 1*b*. In the following, the left side of the housing will be referred to as the proximal side and the right side as the distal side. Two transport devices 2*a* and 2*b* are arranged in the interior of the housing, each having a spindle 3*a*, 3*b* and an externally toothed gear 4*a*, 4*b*. The spindles 3*a*, 3*b* and the externally toothed gears 4*a*, 4*b* of the transport devices 2*a* and 2*b* are each carried by a common shaft 5*a* and 5*b*, respectively.

An adapter 6 is also arranged inside the housing 1, said adapter having two internal threads 7*a* and 7*b* in which the spindles 3*a* and 3*b* of the transport directions engage. The spindles 3*a* and 3*b* can be fixedly mounted in the proximal region of the housing and loosely mounted in the distal region.

The adapter 6 has an element 8 which protrudes through an incision 9 in the upper shell 1*a* of the housing so that it is visible from the outside on the upper shell 1*a*. The upper shell 1*a* has a scale 10 along the incision 9. If the adapter 6 is displaced inside the housing, the element 8 is displaced along the scale 10, so that the position of the adapter 6 can be read on the scale 10.

The housing has in its interior a wall 11 which delimits a proximal portion of the housing towards the distal side. The shafts 5a and 5b of the transport devices 2a, 2b pass through the wall 11. The externally toothed gears 4a, 4b of the transport devices 2a, 2b are then on the distal side of the wall 11.

The spindles 3a, 3b are arranged in the proximal region of the housing. By rotating the spindles 3a, 3b, the adapter 6 can be displaced in this region of the housing between the proximal end of the housing and the wall 11.

An internally toothed gear 12 is arranged in a region of the housing distal to the wall 11. In this region, the housing has two openings 13a and 13b through which the internally toothed gear 12 protrudes. The internally toothed gear 12 can be rotated from the outside through the openings 13a and 13b.

The externally toothed gears 4a and 4b of the transport devices 2a and 2b are in engagement with the internal teeth of the internally toothed gear 12. Inside the internally toothed gear 12, there is also a counter gear 14 which is in engagement with both externally toothed gears 4a, 4b of the transport devices 2a, 2b. The counter gear 14 is coaxial with a cylinder axis of the internally toothed gear 12. A hypotube 15 runs inside the housing in such a way that it is exactly midway between the transport devices 2a and 2b. The adapter 6 has a through opening 17 midway between the internal threads 7a, 7b, through which the hypotube 15 runs, so that the adapter 6 can be displaced along the hypotube 15.

The device shown in FIG. 1 has an inner catheter 16 which partially runs inside the hypotube 15. The catheter 16 is glued to the hypotube 15 at its distal end.

The adapter 6 is connected to a sheath 18 on its proximal side. The connection between the sheath 18 and the adapter 6 can be established, for example, via a screw cap 20 and a stainless-steel ring with a chamfer 19. A socket 21 can be provided around the screw cap 20 and the stainless-steel ring 19 as protection against bending and kinking and for the exact guidance of the sheath 18 when it is removed.

To secure the housing against rotation and transport, a stopper 22 can be provided which, for example, can be inserted through the incision 9 and blocks movement of the adapter 6 in the inserted state. For this purpose, the stopper 22 can have, for example, pegs which engage in corresponding openings on the top of the upper shell 1a.

The hypotube 15 can be inserted at its distal end into a wing component 23, which lies in a region delimiting the housing in the distal direction.

Figure 2:
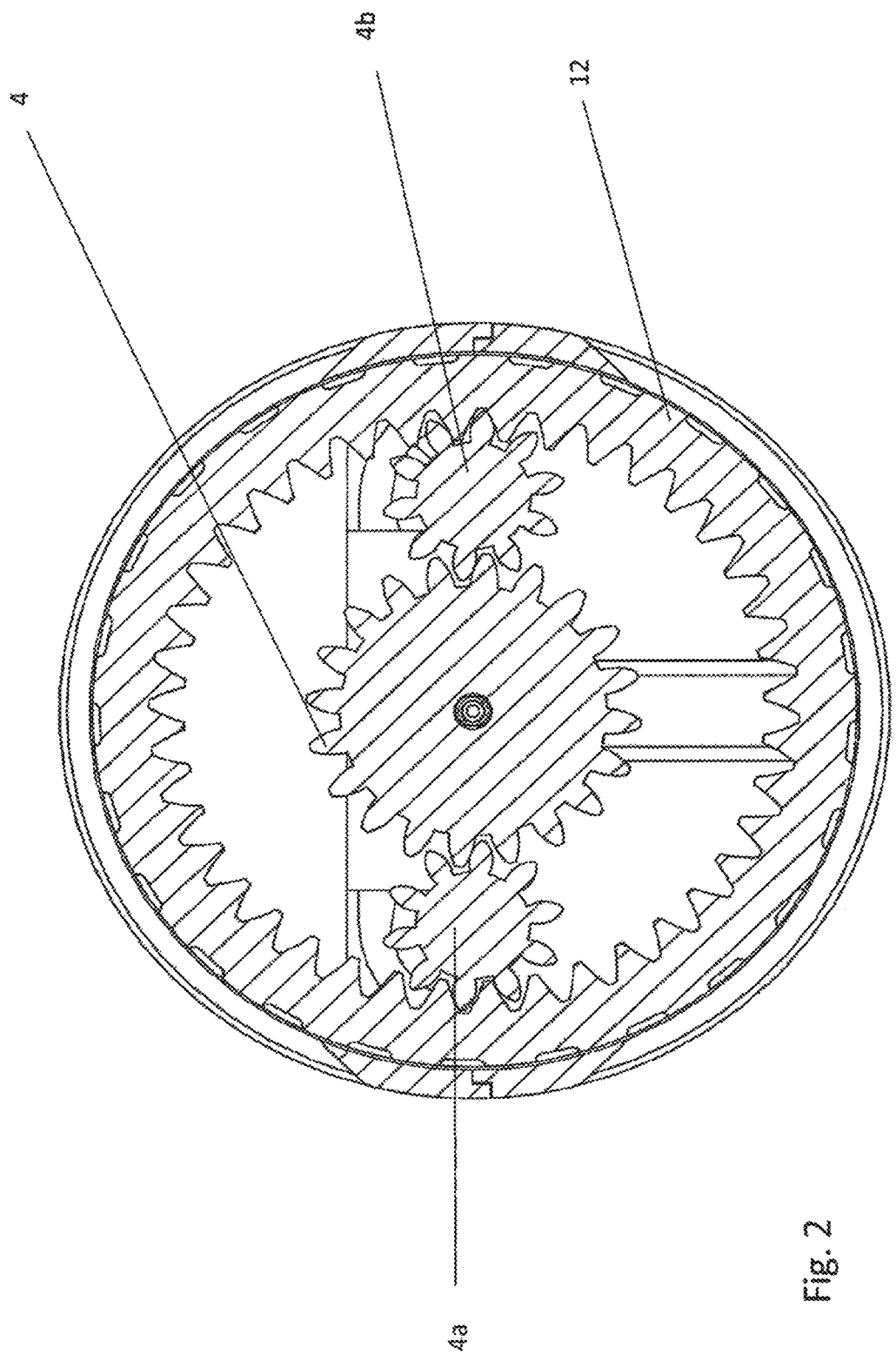
FIG. 2 is a section through an internally toothed gear with externally toothed gears and a counter gear.

FIG. 2 is a section through the implantation device according to the invention of FIG. 1 in the region of the internally toothed gear 12. The section plane lies perpendicular to the longitudinal directions of the shafts 5a, 5b of the transport devices 2a, 2b.

If the internally toothed gear 12 is rotated clockwise by a user as shown, then the externally toothed gears 4a, 4b of the transport devices 2a, 2b also rotate clockwise. The centrally arranged counter gear 4 is in engagement with the gears 4a, 4b and in this case rotates counterclockwise. The torque can be transmitted between the gears 4a, 4b through the counter gear 14.

In the example shown, the internally toothed gear 12 has 40 teeth and the two externally toothed gears 4a, 4b each have 10 teeth. The gear ratio in the example shown is 4 and all teeth have a pressure angle of 20°.

If the length of the implant is 100 mm, it is advantageous if the path covered by the sheath 18 during implantation is at least 100 mm. In the example shown, the pitch of the thread flanks of the spindles 3a, 3b was set to 6 mm to cover this distance. In combination with the selected transmission ratio of the toothed gearing, a complete discharge of the implant with 4.16 revolutions of the internally toothed gear 12 is possible. The thread of the spindle can be designed as a trapezoidal thread, which is particularly suitable for the transmission of movements and forces.

The scale 10 on the visible surface of the upper shell 1a in centimeters is used to read the process path covered.

The implantation device of the invention can be used, for example, to discharge peripheral stents, to discharge several peripheral stents with defined spacings and to discharge stent grafts. In particular, it can be used to discharge vascular and cardiovascular implants.

The implantation device according to the invention enables an implant to be easily positioned and to be discharged in a slip-free manner with higher force and torque transmission than is possible with systems of the prior art. By reducing the expenditure of force, the risk of the catheter moving relative to the sheath during the implantation process is reduced.

The catheter system can be flushed via a Luer-Lock connector in the adapter 6. A guide wire, on the other hand, can be pushed through the wing element 23.

Figure 3:
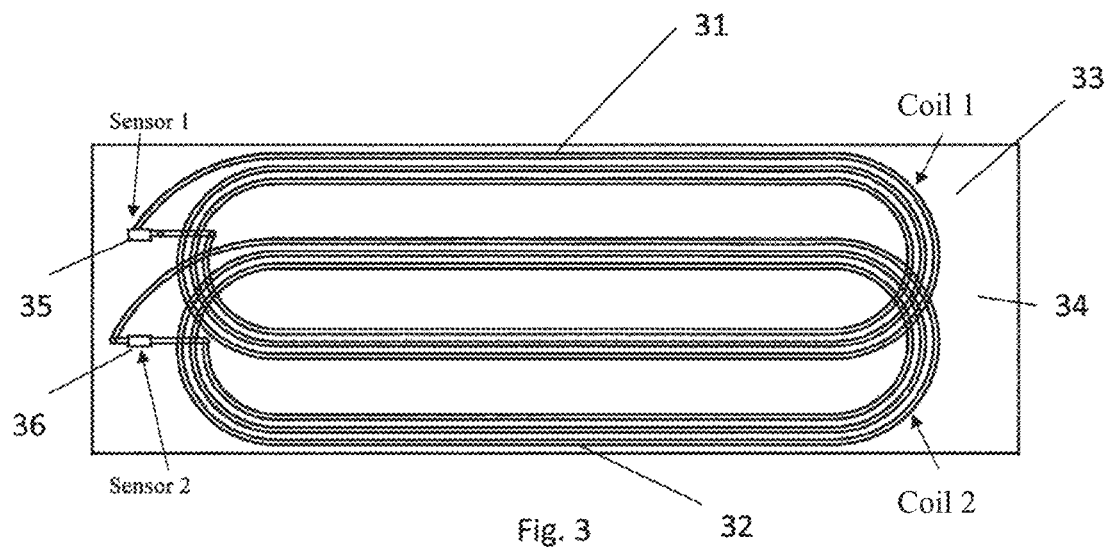
FIGS. 3 and 4 are examples of a sensor implant which can be implanted with the implantation device according to the invention.

FIG. 3 shows an example of a sensor implant which can be implanted with the implantation device according to the invention. The sensor implant comprises a printed circuit 33 with a first conductor loop structure 31 and a second conductor loop structure 32. The conductor loop structure 31 is applied to a front side of a substrate 34, facing the viewer in FIG. 3, and the second conductor loop structure 32 is applied to a rear side of the substrate 34 facing away from the viewer. The substrate 34 thus electrically isolates the first conductor loop structure 31 and the second conductor loop structure 32 from one another.

The conductor loop structures 31 and 32 each have three coils in the example shown. Each of the conductor loop structures 31 and 32 has two straight regions which are parallel to one another and are connected to one another via two circularly curved regions. In the straight regions, the conductor paths run parallel to one another and straight and in the circularly curved regions, the conductor paths run along a circular line and parallel to one another for all coils of the same conductor loop structure. A first capacitive pressure sensor 35 is coupled to the first conductor loop structure 31. The capacitive pressure sensor 35 is coupled between the two ends of the conductor loop structure 31. Correspondingly, the conductor loop structure 32 has a second capacitive pressure sensor 36, which in turn is arranged between the two ends of the conductor loop structure 32. The first capacitive pressure sensor 35 forms with the first conductor loop structure 31 a first resonant circuit with a first resonance frequency. The second capacitive pressure sensor 36 forms with the second conductor loop structure 32 a second resonant circuit with a second resonance frequency.

The first conductor loop structure 31 is wound around a winding axis, wherein the winding axis here penetrates the center point of the conductor paths of the conductor loop structure 31 and is perpendicular to the substrate 34, In a corresponding manner, the conductor paths of the second conductor loop structure 32 are wound around a second coil axis, which in turn runs through the center of the conductor path of the second conductor loop structure 32 and is perpendicular to the substrate 34.

Figure 4:
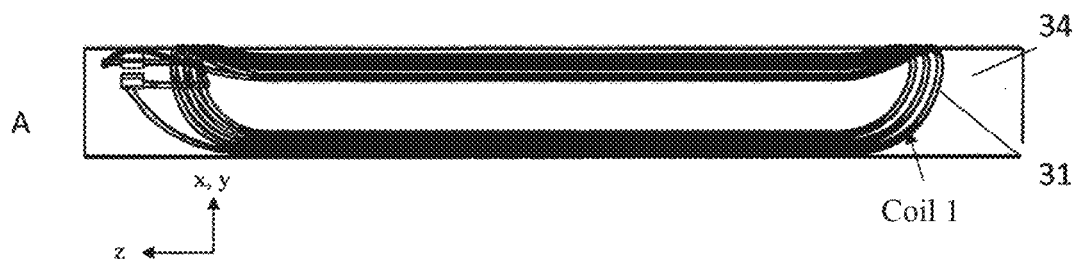
Figure 4:
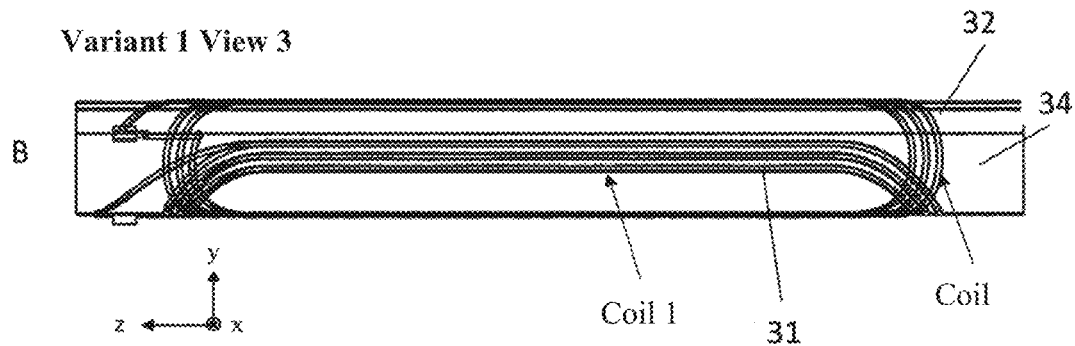

An implant as shown in FIG. 4 can be produced from the structure shown in FIG. 3 by bending the substrate 34 about an axis which runs parallel to the longitudinal sides of the substrate 34, which are parallel to the straight portions of the conductor loop structures 31 and 32. This direction will be referred to below as the Z direction.

FIG. 4A shows this embodiment of the transponder in a first direction which is perpendicular to the Z direction and at an angle of 45° to the X-axis and the Y-axis. Section FIG. 4B shows the transponder viewed in the direction of the X-axis.

The conductor loop structures 31 and 32 can advantageously be dimensioned such that, when the substrate 34 is bent in the manner described, the straight regions of the conductor loop structures are exactly diametrically opposite one another with respect to the axis about which the substrate 34 was bent. The substrate 34 is preferably bent into a circular shape in such a way that the coil axes of the first conductor loop structure and the second conductor loop structure 32 are at the desired angle to one another, preferably perpendicular to one another. The implantation device according to the invention is suitable for the implantation of such an implant.

The invention claimed is:

1. An implantation device for implanting a vascular implant, comprising
    an internally toothed gear,
    one or more transport devices arranged adjacent to one another, each with a spindle and an externally toothed gear arranged coaxially to the spindle, which is firmly connected to the spindle,
    at least one adapter with a number of threads corresponding to the number of transport devices,
    wherein the gears of the one or more transport devices are in engagement with the internal thread of the internally toothed gear,
    and wherein the spindles of the one or more transport devices are each in engagement with one of the threads of the adapter, further comprising
    a tubular sheath which is connected at one of its ends to the adapter,
    a hypotube which is arranged over at least the length of the spindles, adjacent to the spindles of the one or more transport devices and parallel to them,
    and a catheter which is at least partially arranged within the hypotube.

2. The implantation device according to claim 1,
    wherein the internally toothed gear, the one or more transport devices and the adapter are arranged in a common housing,
    wherein the hypotube is held at a distal end of the housing and extends at least to an opposite proximal end of the housing and
    wherein the catheter is connected to the end of the hypotube at which the hypotube is held on the housing.

3. The implantation device according to claim 2, wherein the housing has at least two openings through which the internally toothed gear protrudes and can be rotated.

4. The implantation device according to claim 2, wherein the housing has a linear scale on an outer face, and wherein the adapter has an element which protrudes through an incision in the housing that extends parallel to the scale, adjacent to the scale.

5. The implantation device according to claim 1, wherein the hypotube is inserted into a wing element at the end at which it is held on the housing.

6. The implantation device according to claim 1, wherein the internal toothing of the internally toothed gear has 40 teeth, and wherein the gear(s) of the one or more transport devices each have 10 teeth.

7. The implantation device according to claim 1, further comprising a counter gear which is arranged inside the internally toothed gear and in engagement with the teeth of the gears of the transport devices.

8. The implantation device according to claim 7, wherein the counter gear is arranged coaxially to an axis of rotation of the internally toothed gear.

9. The implantation device according to claim 1, comprising exactly two transport devices which are arranged opposite each other with respect to the hypotube.

10. The implantation device according to claim 1, wherein the length of the spindles is in each case equal to or greater than 100 mm.

11. The implantation device according to claim 1, wherein the pitch of the spindles is 6 mm.

12. The implantation device according to claim 1, wherein the spindle is designed as a trapezoidal thread.

* * * * *